United States Patent [19]

Alberts et al.

[11] Patent Number: 4,997,658
[45] Date of Patent: Mar. 5, 1991

[54] METHOD FOR ENHANCING THE LOWERING OF PLASMA CHOLESTEROL LEVELS

[75] Inventors: Alfred W. Alberts, Princeton, N.J.; Edward M. Scolnick, Wyneewood, Pa.; Arnold J. Repta, Lawrence, Kans.

[73] Assignee: Merck & Co., Inc., Rahway, N.J.

[21] Appl. No.: 274,173

[22] Filed: Nov. 21, 1988

[51] Int. Cl.$^5$ .............................................. A61K 9/24
[52] U.S. Cl. ..................... 424/473; 514/460
[58] Field of Search .................... 424/473; 514/460

[56]  References Cited

U.S. PATENT DOCUMENTS

| 3,538,214 | 11/1970 | Polli et al. | 424/19 |
|---|---|---|---|
| 3,845,770 | 11/1974 | Theeuwes et al. | 128/260 |
| 3,916,899 | 11/1975 | Theeuwes et al. | 128/260 |
| 4,160,452 | 7/1979 | Theeuwes | 128/260 |
| 4,200,098 | 4/1980 | Ayer et al. | 128/260 |
| 4,256,108 | 3/1981 | Theeuwes | 128/260 |
| 4,285,987 | 8/1981 | Ayer et al. | 427/3 |
| 4,327,725 | 11/1970 | Polli et al. | 424/19 |
| 4,612,008 | 9/1986 | Wong et al. | 604/892 |
| 4,755,180 | 7/1988 | Ayer et al. | |
| 4,863,957 | 9/1989 | Neuenschwander et al. | 514/460 |
| 4,892,884 | 1/1990 | Neuenschwander et al. | 514/570 |
| 4,900,754 | 2/1990 | Regan et al. | 514/460 |

Primary Examiner—Merrell C. Cashion, Jr.
Assistant Examiner—Leon R. Horne
Attorney, Agent, or Firm—Melvin Winokur; Joseph F. DiPrima

[57]  ABSTRACT

The instant invention is directed to a method for enhancing the lowering of plasma cholesterol level in a subject in need thereof which comprises the time-controlled administration of a nontoxic therapeutically effective amount of an HMG-CoA reductase inhibitor to said subject which surprisingly affords an equivalent or improved reduction of plasma cholesterol levels while significantly reducing the amount of HMG-CoA reductase inhibitor circulating in the bloodstream of the subject as compared to the same parameters when the oral administration of a conventional rapid release dosage form is utilized.

10 Claims, No Drawings

METHOD FOR ENHANCING THE LOWERING OF PLASMA CHOLESTEROL LEVELS

BACKGROUND OF THE INVENTION

Hypercholesterolmia is known to be one of the prime risk factors for atherosclerosis and coronary heart disease, the leading cause of death and disability in Western countries.

There are agents known, however, that are very active antihypercholesterolemic agents which function by limiting cholesterol biosynthesis via inhibiting the enzyme, HMG-CoA reductase. These agents include the natural fermentation products, such as mevastatin, lovastatin and pravastatin, and semisynthetic analogs, such as simvastatin.

MEVACOR ®, which contains lovastatin as the active agent, and ZOCOR ®, which contains simvastatin as the active agent, are now commercially available for use as antihypercholesterolemic drugs. The reduction of the effective dosage amount which is anticipated to diminish the incidence of adverse experience associated which these drugs would be extremely beneficial in view of the lifetime regimen of treatment of hypercholesterolemia.

Antihypercholesterolemic agents are useful for the treatment of arteriosclerosis, atherosclerosis, hyperlipidemia, familial hypercholesterolemia and like diseases in humans. They may be administered orally or parenterally in the form of a capsule, a tablet, an injectable preparation or the like. It is usually desirable to use the oral route. Doses may be varied, depending on the age, severity of hypercholesterolemia, body weight and other conditions of human patients but daily dosage for adults is within a range of from about 2 mg to 2000 mg (preferably 10 to 100 mg) which may be given in two to four divided doses. Higher doses may be favorably employed as required.

Utilizing controlled or sustained release technologies, a single administration of the indicated daily dosage amount delivers the drug to the patient over an extended period of time (i.e. 6 to 24 hours) to yield an equivalent or improved therapeutic effect while lowering the peak drug plasma levels. The response is apparently effected by improved hepatic extraction of the absorbed drug as the liver is the site of action of these antihypercholesterolemic agents. An additional benefit of this approach is the potential reduction in side effects associated with circulating drug.

Controlled delivery devices for the sustained release of therapeutically active agents are well known in the art. Generally, these devices may be characterized as either diffusion controlled systems, osmotic dispensing devices, dissolution controlled matrices, or erodible/degradable matrices.

U.S. Pat. No. 3,538,214 discloses a diffusion controlled device in which a tablet core containing an active ingredient is surrounded by a water insoluble coating which contains a film modifying agent soluble in the external fluids in the gastrointestinal tract.

An example of an osmotic device is described in U.S. Pat. Nos. 3,845,770 and 3,916,899 which is a core composition of an active agent and an osmotically effective solute which is enclosed by an insoluble semipermeable wall having a release means. Numerous modifications to these types of delivery devices have been described in the art in an effort to improve their release characteristics. U.S. Pat. Nos. 4,256,108; 4,160,452; 4,200,098, 4,285,987, 4,327,725, and 4,612,008 disclose such improved delivery devices.

Co-pending U.S. patent applications Ser. Nos. 073,781 and 073,596, filed July 15, 1987 disclose systems which comprise an inner core compartment of osmotically active composition surrounded by an enclosing controlled porosity wall material that is substantially permeable to both solute and external fluid. These systems are osmotic dispensing devices for a broad range of therapeutically active agents. Co-pending U.S. patent application Ser. No. 100,644, filed Sept. 24, 1987 discloses such a delivery system which is controlled through the influence of a controlled release solubility modulator contained within the drug delivery device. Co-pending U.S. patent application Ser. No. 081,090, filed Aug. 3, 1987 also discloses such a delivery system which is controlled through the influence of a water insoluble, non-diffusible charged resin entity contained within the drug delivery device.

U.S. Pat. No. 4,755,180 discloses a dosage form comprising a beneficial agent and a polymer coated osmotically effective solute for regulating the solubility of the beneficial agent.

Numerous examples of diffusion controlled and erodible/degradable devices are discussed in detail in Controlled Drug Delivery: Fundamentals and Applications, 2nd Edition, J. R. Robinson and V. H. L. Lee, Eds., Marcel Dekker, Inc., New York and Basel, 1987, and in Controlled Drug Delivery: Basic Concepts, Vols. I and II, S. D. Brunk, Ed., CRC Press Inc, Boca Raton, Fla., 1983.

BRIEF DESCRIPTION OF THE INVENTION

The instant invention is directed to a method for enhancing the lowering of plasma cholesterol levels in a subject in need thereof which comprises the time-controlled adminstration of a nontoxic therapeutically effective amount of an HMG-CoA reductase inhibitor to said subject which surprisingly affords an equivalent or improved reduction of plasma cholesterol levels while significantly reducing the amount of HMG-CoA reductase inhibitor circulating in the bloodstream of the subject and thereby reducing the subject's peripheral of non-liver exposure to the inhibitor as compared to the same parameters when the oral adminstration of a conventional rapid release dosage form is utilized.

DETAILED DESCRIPTION OF THE INVENTION

This invention concerns a method for enhancing the lowering of plasma cholesterol levels in a subject in need thereof which comprises the time-controlled administration of a non-toxic therapeutically effective amount of an HMG-CoA reductase inhibitor to said subject utilizing a drug-delivery device for the controlled release of a therapeutically active ingredient into an enviornment of use.

The expression "time-controlled administration" as used herein broadly defines the controlled release of the HMG-CoA reductase inhibitor, in either the active form or pro-drug form, into the enviornment of use over a period of six (6) to twenty-four (24) hours. The time-controlled administration of the therapeutic effective amount of an HMG-CoA reductase inhibitor may be achieved by a variety of pharmaceutical procedures known to those skilled in the art. Among those procedures, but not inclusive, are diffusion controlled systems, osmotic devices, dissolution controlled matrices and erodible/degradable matrices.

One class of drug delivery device that is employed in the instant method includes the drug delivery devices which comprise a core composition comprising (a) a diffusible water soluble HMG-CoA reductase inhibitor, and (b) an osmotically effective agent surrounded by either (a) a water insoluble wall prepared to water but substantially impermeable to solute and (ii) 0.1 to 75% by weight, based on the total weight of (i) and (ii), of at least one water leachable pore forming additive dispersed throughout said wall; or (b) a substantially imperforate water insoluble wall surrounding said core composition and prepared from a semipermeable material substantially impermeable to core composition and permeable to the passage of an external fluid in the enviornment of use, with said wall (b) having a means for release of the therapeutic agent through the water insoluble wall.

Illustrative of this class of drug delivery device are those devices wherein the core composition of the drug delivery device comprises (a) a water insoluble, nondiffusible charged resin entity, and (b) a diffusible water soluble ionizable HMG-CoA reductase inhibitor carrying the same charge as said resin entity.

Also, illustrative of this class of drug delivery device are those wherein the core composition of the drug delivery device comprises (a) a solubility modulating agent which is either (i) surrounded by a water insoluble coat containing at least one pore forming additive dispersed throughout said coat, or (ii) dispersed in a matrix substrate, and (b) a diffusible water soluble HMG-CoA reductase inhibitor.

The HMG-CoA reductase inhibitors which are utilized in the instant method include the compounds represented by the following structural formulae (I) and (II):

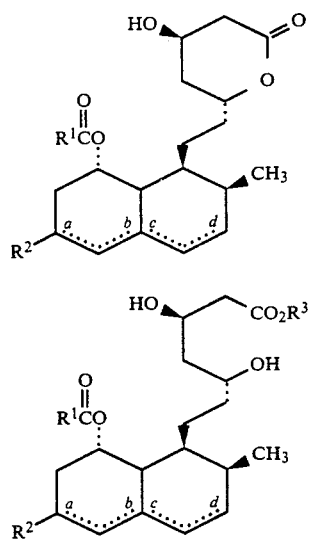

wherein:
$R^1$ is:
(1) $C_{1-10}$ alkyl;
(2) substituted $C_{1-10}$ alkyl in which one or more substituent(s) is selected from
   (a) hydroxy,
   (b) $C_{1-5}$ alkoxycarbonyl,
   (c) $C_{1-5}$ acyloxy,
   (d) $C_{3-8}$ cycloalkyl, and
   (e) phenyl and;
(3) $C_{3-8}$ cycloalkyl;
$R^2$ is:
(1) methyl;
(2) substituted $C_{1-10}$ alkyl in which the substituent is selected from:
   (a) hydroxy, or
   (b) $C_{1-5}$ acyloxy, and
(3) $C_{1-5}$ alkoxycarbonyl and;
(4) hydroxy; and
$R^3$ is:
(a) hydrogen;
(b) $C_{1-5}$ alkyl;
(c) substituted $C_{1-5}$ alkyl in which the substituent is selected from
   (i) phenyl,
   (ii) dimethylamino, and
   (iii) acetylamino, and
(d) 2,3-dihydroxypropyl;
a, b, c and d each represent single bonds or one of a, b, c and d represents a double bond or both a and c or both b and d represent double bonds, provided that when a is a double bond, $R^2$ is methyl, substituted $C_{1-10}$ alkyl or $C_{1-5}$ alkoxycarbonyl; or
a pharmaceutically acceptable salt thereof.

The compounds represented by structural formula (I), and structural formula (II) wherein $R^3$ is other than hydrogen have been described as the pro-drug form of the active moiety, the compounds represented by structural formula (II) wherein $R^3$ is hydrogen.

One class of these HMG-CoA reductase inhibitor are those compounds of formula (I) or (II) wherein:
$R^1$ is $C_{1-10}$ alkyl; and
$R^2$ is
(1) methyl; or
(2) hydroxy.

Illustrative of this class of compounds are those selected from the group consisting of
(1)  7-[1,2,6,7,8,8a(R)-hexahydro-2(S),6(R)-dimethyl-8(S)-(2,2-dimethylbutyryloxy)-naphthalenyl-1(S)]-3(R),5(R)-dihydroxyheptanoic acid;
(2)  7-[1,2,6,7,8,8a(R)-hexahydro-2(S),6(R)-dimethyl-8(S)-(2(S)-methylbutyryloxy)-naphthalenyl-1(S)]-3(R),5(R)-dihydroxyheptanoic acid;
(3)  7-[1,2,6,7,8,8a(R)-hexahydro-2(S)-methyl 6(R)-hydroxy-8(S)-(2(S)-methylbutyryloxy)-naphthalenyl-1(S)]-3(R),5(R)-dihydroxyheptanoic acid; and
(4)  7-[1,2,6,7,8,8a(R)-hexahydro-2(S)-methyl 6(S)-hydroxy-8(S)-(2(S)-methylbutyryloxy)-naphthalenyl-1(S)]-3(R),5(R)-dihydroxyheptanoic acid or a pharmaceutically acceptable salt thereof, specifically the tris(hydroxymethyl)methylammonium salt.

Also illustrative of this class of compounds are those selected from the group consisting of
(1)  6(R)-[2-[8(S)-(2(S)-methylbutyryloxy)-2(S),6(R)-dimethyl-1,2,6,7,8,8a(R)-hexahydronaphthtyl-1(S)]ethyl]-4(R)-hydroxy-3,4,5,6-tetrahydro-2H-pyran-2-one (generically known as lovastatin); and
(2)  6(R)-[2-[8(S)-(2,2-dimethylbutyryloxy)-2(S),6(R)-dimethyl-1,2,6,7,8,8a(R)-hexahydronaphthtyl-1(S)]ethyl]-4(R)-hydroxy-3,4,5,6-tetrahydro-2H-pyran-2-one (generically known as simvastatin).

The HMG-CoA reductase inhibitors which are utilized in the instant method are conveniently prepared according to known procedures specifically described in the literature. For example, U.S. Pat. Nos. 4,231,938, 4,342,767, 4,444,784, and 4,346,227 disclose lovastatin, simvastatin and the ring opened dihydroxy acids thereof and pravastatin.

The drug-delivery devices which can be utilized in the method of this invention are conveniently prepared according to known procedures also specifically disclosed in the literature by utilizing the above described HMG-CoA reductase inhibitor as the active agent. For example, U.S. Pat. Nos. 3,845,770, 3,916,899, 4,256,108; 4,160,452; 4,200,098, 4,285,987, 4,327,725, and 4,612,008 and co-pending U.S. patent application Ser. Nos. 073,781 and 073,596, filed July 15, 1987, Ser. No. 100,644, filed Sept. 24, 1987 and Ser. No. 081,090, filed Aug. 3, 1987.

The following examples illustrate the method of the claimed invention and the preparation of one type of the drug-delivery devices which may be utilized in the method of this invention and as such are not to be considered as limiting the invention set forth in the claims appended hereto.

EXAMPLE 1

7-[1,2,6,7,8,8a(R)-hexahydro-2(S),6(R)-dimethyl-8(S)-2(2,2-dimethylbutyryloxy)-naphthalenyl-1(S)]-3(R)-dihydroxyheptanoic acid, an HMG-CoA reductase inhibitor which is the ring opened dihydroxy acid of simvastatin, was administered to dogs as the ammonium salt as either as oral bolus dose (rapid release) or as a continuous gastric infusion over 24 hours (simulated controlled release). In both cases, each dog received a dose of 10 mg/kg/day for 28 days of the above named HMG-CoA reductase inhibitor. Plasma cholesterol was determined throughout the entire study and drug-treatment levels compared to control cholesterol levels (pre dosing) for each dog. Circulating plasma levels of the above named HMG-CoA reductase inhibitor were determined on Day 16 of each drug dosing period. The results are shown in Table 1.

TABLE 1

Plasma Cholesterol and Inhibitor Levels Following Oral Rapid Release and Gastric Infusion in Dogs.

| | Mean Maximum Reduction In Plasma Cholesterol (percent, mean ± SD) | Peak Circulating Plasma Drug Level (ng/ml, mean ± SD) |
|---|---|---|
| Rapid Release | 31[a] | 3575[a] |
| Gastric Infusion | 60 ± 4.0[b] | 75 ± 12.5[b] |

[a] n = 1 dog
[b] n = 4 dogs

It is clear from the results (Table 1) that gastric infusion (simulated controlled-release) of the above named HMG-CoA reductase inhibitor affords improved lowering of cholesterol levels while resulting in decreased circulating levels of drug when compared to rapid release administration.

EXAMPLE 2

The same HMG CoA reductase inhibitor of Example 1 was administered to dogs as either an oral bolus dose (dry-fill capsule, rapid release) or as an oral controlled-release preparation. In both cases, each dog received a total daily dose of 100 mg equivalents of above named HMG-CoA reductase inhibitor. The resin modulated osmotic drug delivery device as prepared in Example 3, below, afforded controlled in vitro release of the drug over a 6–10 hour period. Serum cholesterol was determined throughout the entire study and drug-treatment levels compared to control cholesterol levels (pre-dosing) for each dog. Circulating inhibitor levels were determined on Day 16 of each drug dosing period. The results are shown in Table 2.

TABLE 2

Serum Cholesterol and Plasma Drug Levels Following Oral Rapid-Release and Controlled-Release of in Dogs

| Dog No. | Percent Reduction in Serum Chloesterol | | Peak Circulating Plasma Drug Level (ng/ml) | |
|---|---|---|---|---|
| | Rapid Release | Controlled Release | Rapid Release | Controlled Release |
| 01 | 8 | 26 | 571 | 203 |
| 03 | 20 | 30 | 1946 | 213 |
| 37 | 24 | 44 | 249 | 273 |
| 66 | 8 | 23 | 565 | 127 |
| 81 | 22 | 40 | 652 | 113 |
| 84 | 16 | 20 | 989 | 187 |
| 85 | 15 | 35 | 3940 | 319 |

These results (Table 2) indicate that controlled-release administration of above named HMG-CoA reductase inhibitor results in a consistent improvement in cholesterol lowering while significantly reducing circulating drug levels when compared to conventional rapid release oral bolus dosing.

EXAMPLE 3

A plurality of drug-delivery systems containing the HMG-CoA reductase inhibitor, 7-[1,2,6,7,8,8a(R)-hexahydro-2(S),6(R)-dimethyl-8(S)-(2,2-dimethylbutyryloxy)naphthalenyl-1(S)]-3-(R),5(R)-dihydroxybutyryloxy)naphthalenyl-1(S)]-3-(R),5(R)-dihydroxyhepanoate tris(hydroxymethyl)methylammonium salt, and Dowex 50X 8–100, and a negatively charged resin were prepared. A wet granulation was made containing 7-[1,2,6,7,8,8a(R)-hexahydro-2(S),6(R)-dimethyl-8(S)-(2,2-dimethylbutyryloxy)-naphthalenyl-1(S)]-3(R),5(R)-dihydroxyhepanoate tris(hydroxymethyl)methylammonium salt:tromethamine free base:mannitol:Dowex 50X 8–100:polyvinylpyrrolidone: butylated hydroxyanisole mixed in a 1:4.13:3.94:1.97:0.98:0.0024 ratio. The dried granules were lubricated with magnesium stearate (0.5% w/w) and compressed into 305 mg core compartments with a ⅜″ standard concave tabletting die on a Stokes F-press tabletting machine. Next, a 350 μm thick microporous coat (54 g) having the acetyl content of 39% and 18 g cellulose acetate having an acetyl content of 32% were dissolved in a dichloromethane/methanol solvent blend. To this was added 52 g sorbitol and 14.4 g polyethylene glycol 400 dissolved in a water/methanol solvent blend. The composite solution contained water:methanol: dichloromethane in an approximate 1:10:15 ratio. This solution was sprayed onto cores in a Uni-Glatt fluidized bed coating machine. The in vitro release of 7-[1,2,6,7,8,8a(R)-hexahydro-2(S),6(R)-dimethyl-8(S)-(2,2-dimethylbutyryloxy)-naphthalenyl-1(S)]-3(R),5(R)-dihydroxyhepanoate tris(hydroxymethyl)-methylammonium salt from these devices into 900 ml volumes of 37° C., pH 1.2 HCl buffer and pH 8.0 phosphate buffer, both made isotonic with sodium chloride, was monitored using a USP Dissolution Method #2 apparatus with constant stirring at 50 rpm. Devices evaluated at pH 1.2 were transferred after 4 hours into the pH 8 media to simulate the variable pH conditions of the human gastrointestinal tract. HPLC was used to assay for drug. The release of 7-[1,2,6,7,8,8a(R)-hexahydro-2(S),6(R)-dimethyl-8(S)-(2,2-dimethylbutyryloxy)-naphthalenyl-1(S)]-3(R),5(R)-dihydroxyheptanoate tris(hydroxymethyl)-methylammonium salt was prolonged for >14 hours with approximately 70% released at a nearly constant rate.

EXAMPLE 4

Core tablets were prepared as described in Example 3 substituting the anionic resin Amberlite IRP-64 for Dowex 50X 8-100. Cores (300 mg) were compressed in a ⅜" standard concave tabletting die on a Stokes F-press. A micro-porous coating was applied to the cores by fluidizing bed coating techniques. The coating solution was prepared in a water:methanol:methylene chloride (1:10:15) cosolvent containing 54 g cellulose acetate 398-30, 18 g cellulose acetate 320S, 52 g sorbitol, and 7.2 g polythyene glycol 400. A microporous wall approximately 370 μm thick was applied.

EXAMPLE 5

A plurality of drug delivery systems containing Amberlite IRP-64 as a negatively charged resin are prepared as follows: a wet granulation is made containing the HMG-CoA reductase inhibitor, 7-[1,2,6,7,8,8a(R)-hexahydro-2(S),6(R)-dimethyl-8(S)-(2,2-dimethyl-butyryloxy)-naphthalenyl-1(S)]-3(R),5(R)-dihydroxyheptanoate tris(hydroxymethyl)methylammonium salt, troethamine, mannitol, Amberlite IRP-64, polyvinylpyrrolidone, and butylated hydroxyanisole mixed 1:4:4:2:1:0.003, respectively. Core tablets are prepared by compressing 300 mg aliquots of the dried granulation into a ⅜" standard concave tabletting die with a single station Stokes F-press. Next, a semipermeable wall is applied to these cores. Cellulose acetate (18 g) having an acetyl content of 32% and 54 g of cellulose acetate having an acetyl content of 39% are dissolved in a dichloromethane/methanol solvent blend. To this is added 20 g polyethylene glucol 400 as a flux enhancer/plasticizer dissolved in a water/methanol solvent blend. The composite solution contains water:methanol:dichloromethane in an approximate 1:10:15 ratio. This solution is sprayed onto the cores in a commerical Uni-Glatt fluidized bed coating machine. A wall 100 to 200 microns thick is applied. A hole 0.15 mm in diameter is drilled through the semipermeable wall to provide a means of release for the core composition.

EXAMPLE 6

A plurality of drug delivery devices are prepared with the HMG-CoA reductase inhibitor, 7-[1,2,6,7,8,8a(R)-hexahydro-2(S),6(R)-dimethyl-8(S)-(2(S)-methylbutyryloxy)-naphthalenyl-1(S)]-3(R),5(R)-dihydroxyhepanoate tris(hydroxymethyl)methylammonium salt and the negatively charged insoluble resin amberlite IRP-64. A wet granulation is made containing 7-[1,2,6,7,8,8a(R)-hexahydro-2(S),6(R)-dimethyl-8(S)-(2(S)-methylbutyryloxy)-naphthalenyl-1(S)]-3(R),5(R)-dihydroxyhepanoate tris(hydroxymethyl)mathylammonium salt, tromethamine, mannitol, Amberlite IRP-64, polyvinylpyrrolidone, and butylated hydroxyanisole mixed 1:4:4:2:1:0.003, respectively. Core compartments are made by compressing 300 mg aliquots of the dried granules into a ⅜" standard concave tabletting dye as in Example 3. Next, a microporous wall is applied. Cellulose acetate (36 g) having an acetyl content of 39% and 36 g cellulose acetate having an acetyl content of 32% are dissolved in an acetone/methanol solvent blend. To this is added 54 g nicotinamide as pore former and 40 g polyethylene glycol 400 as a flux enhancer/plasticizer dissolved in methanol. This solution is sprayed onto the cores in a Uni-Glatt fluidized bed coating machine to form a microporous wall 100 microns thick. This microporous wall is then covered by a semiporous wall as described in Example 5 with a hole 0.15 mm in diameter drilled through both the microporous and semipermeable walls.

EXAMPLE 7

A plurality of core tablets are prepared as described in Example 3. These cores are coated with a semipermeable wall 200 microns thick containing a drilled 0.15 mm diameter hole as described in Example 5. The devices are then spray coated with 100 micron thick layer of a water soluble mixture of polyvinylpyrrolidone and sorbitol mixed in a 1:25 weight ratio. This layer is then covered by a microporous wall 100 microns thick by spray coating a dichloromethane:methanol:water: solution of a 1:1:1 blend of cellulose acetate having an acetyl content of 32%, cellulose acetate having an acetyl content of 39%, and sorbitol. The sorbitol is incorporated as a pore forming additive.

What is claimed is:

1. A method for the lowering of plasma cholesterol level in a subject in need thereof which comprises the time-controlled administration over a period of six (6) to twenty-four (24) hours of a nontoxic therapeutically effective amount of about 2 mg to 2000 mg of an HMG-CoA reductase inhibitor, which affords an lowering equivalent or greater lowering of plasma cholesterol levels while reducing the amount of HMG-CoA reductase inhibitor circulating in the bloodstream of the subject when compared to the oral administration of an equivalent dosage of a rapid-release dosage form,

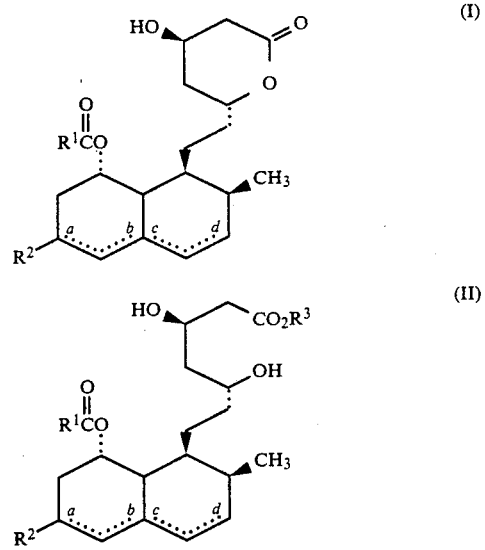

wherein
wherein
the HMG-CoA reductase inhibitor is a compound of the following structural formulae (I) and (II):
R¹ is selected from the group consisting of
(1) C₁₋₁₀ alkyl;
(2) substituted C₁₋₁₀ alkyl in which one or more substituent(s) is
(a) hydroxy,
(b) C₁₋₅ alkoxycarbonyl,
(c) C₁₋₅ acyloxy,
(d) C₃₋₈ cycloalkyl, and
(e) phenyl, and;

(3) $C_{3-8}$ cycloalkyl;
R² is selected from the group consisting of
  (1) methyl;
  (2) substituted $C_{1-10}$ alkyl in which the substituent is
    (a) hydroxy, or
    (b) $C_{1-5}$ acyloxy, and
  (3) $C_{1-5}$ alkoxycarbonyl and;
  (4) hydroxy; and
R³ is selected from the group consisting of
  (a) hydrogen;
  (b) $C_{1-5}$ alkyl;
  (c) substituted $C_{1-5}$ alkyl in which the substituent is
    (i) phenyl,
    (ii) dimethylamino, and
    (iii) acetylamino, and
  (d) 2,3-dihydroxypropyl; a, b, c and d each represent single bonds or one of
a, b, c and d represents a double bond or both a and c or both b and d represent double bonds, provided that when a is a double bond, R² is methyl, substituted $C_{1-10}$ alkyl or $C_{1-5}$ alkoxycarbonyl; or a pharmaceutically acceptable salt thereof.

2. A method of claim 1 wherein
R¹ is $C_{1-10}$ alkyl; and
R² is methyl; or hydroxy.

3. A method of claim 2 wherein the HMG-CoA reductase inhibitor is selected from the group consisting of
  (1) 7-[1,2,6,7,8,8a(R)-hexahydro-2(S),6(R)-dimethyl-8(S)-(2,2-dimethylbutyryloxy-naphthalenyl-1(S)]-3(R),5(R)-dihydroxyheptanoic acid;
  (2) 7-[1,2,6,7,8,8a(R)-hexahydro-2(S),6(R)-dimethyl-8(S)-(2(S)-methylbutyryloxy0-naphthalenyl-1(S)]-3(R)-dihydroxyheptanoic acid; and
  (3) 7-[1,2,6,7,8,8a(R)-hexahydro-2(S)-methyl 6(R)-hydroxy-8(S)-methylbutyryloxy)-naphthalenyl-1(S)]-3(R),5(R)-dihydroxyheptanoic acid; and
  (4) 7-[1,2,6,7,8,8a(R)-hexahydro-2(S)-methyl 6(S)-hydroxy-8(S)-(2(S)-methylbutyryloxu)-naphthalenyl-1(S)]-3(R),5(R)-dihydroxyheptanoic acid.

4. A method of claim 3 wherein the HMG-CoA reductase inhibitor is selected from the group consisting of
  (1) 6(R)-[2-[8(S)-(2(S)-methylbutyryloxy-2(S),6(R)-dimethyl-1,2,6,7,8,8a(R)-hexahydronaphthtyl-1(S)]ethyl]-4(R)-hydroxy-3,4,5,6-tetrahydro-2H-pyran-2-one; and
  (2) 6(R)-[2-[8(S)[(2,2)-dimethylbutyryloxy)-2(S),6(R)-dimethyl-1,2,6,7,8,8a(R)-hexahydronaphthtyl-1(S)]ethyl]-4(R)-hydroxy-3,4,5,6-tetrahydro-2H-pyran-2-one.

5. A method of claim 1 wherein the time-controlled administration is the continuous introduction of the HMG-CoA reductase inhibitor into the enviornment of use over a period of six (6) to twenty-four (24) hours.

6. A method of claim 5 wherein the time-controlled administration of a nontoxic therapeutically effective amount of an HMG-CoA reductase inhibitor is accomplished utilizing a drug-delivery device for the controlled release of the therapeutically active ingredient into an environment of use.

7. A method of claim 6 wherein the drug delivery device is selected from the group consisting of diffusion-controlled systems, osmotic devices, dissolution-controlled matrices and erodible/degradable matrices.

8. A method of claim 7 wherein the drug delivery device comprises;
  (A) a core composition comprising
    (a) a diffusible water soluble HMG-CoA reductase inhibitor, and
    (b) an osmotically effective agent; and
  (B) a water insoluble wall surrounding said core composition and prepared from
    (i) a polymer material that is permeable to water but substantially impermeable to solute and
    (ii) 0.1 to 75% by weight, based on the total weight of (i) and (ii), of at least one water leachable pore-forming additive dispersed throughout said wall; or
  (C) a substantially imperforate water insoluble wall surrounding said core composition and prepared from a semipermeable material substantially impermeable to core composition and permeable to the passage of an external fluid in the enviornment of use, with said wall having a means for release of the therapeutic agent through the water insoluble wall.

9. A method of claim 8 wherein the core composition of the drug delivery device comprises:
  (a) a water insoluble, nondiffusible charged resin entity, and
  (b) a diffusible water soluble ionizable HMG-CoA reductase inhibitor carrying the same charge as said resin entity.

10. A method of claim 9 wherein the core composition of the drug delivery device comprises:
  (a) a solubility modulating agent which is either (i) surrounded by a water insoluble coat containing at least one pore-forming additive dispersed throughout said coat, or (ii) dispersed in a matrix substrate, and
  (b) a diffusible water soluble HMG-CoA reductase inhibitor.

* * * * *

UNITED STATES PATENT AND TRADEMARK OFFICE
CERTIFICATE OF CORRECTION

PATENT NO. : 4,997,658

DATED : March 5, 1991

INVENTOR(S) : A. W. Alberts et al

It is certified that error appears in the above-identified patent and that said Letters Patent is hereby corrected as shown below:

Col. 8, claim 1, at line 27, should read "affords an equivalent lowering or greater lowering of plasma".

Signed and Sealed this

Thirteenth Day of October, 1992

Attest:

DOUGLAS B. COMER

Attesting Officer

Acting Commissioner of Patents and Trademarks